United States Patent
Bedingfield et al.

(10) Patent No.: US 9,180,238 B2
(45) Date of Patent: Nov. 10, 2015

(54) DISTRIBUTED PROCESSING SYSTEM AND METHOD FOR DIALYSIS MACHINES

(75) Inventors: John Bedingfield, Largo, FL (US);
Benjamin Kellam, Dunedin, FL (US);
Ronald D. Baerg, Seminole, FL (US);
Gideon Hecht, Seminole, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 572 days.

(21) Appl. No.: 12/137,459

(22) Filed: Jun. 11, 2008

(65) Prior Publication Data

US 2009/0312694 A1 Dec. 17, 2009

(51) Int. Cl.
*A61M 1/00* (2006.01)
*A61M 1/16* (2006.01)

(52) U.S. Cl.
CPC .......... *A61M 1/1656* (2013.01); *A61M 1/1664* (2013.01); *A61M 2205/3368* (2013.01); *A61M 2205/50* (2013.01); *A61M 2205/502* (2013.01)

(58) Field of Classification Search
CPC ............ A61M 1/1656; A61M 1/1664; A61M 2205/50; A61M 2205/502
USPC ................. 604/29, 65–67; 236/1 B; 700/2–7; 237/2 A; 165/208, 209
See application file for complete search history.

(56) References Cited

U.S. PATENT DOCUMENTS

| | | | |
|---|---|---|---|
| 4,263,647 A | 4/1981 | Merrell et al. | |
| 4,370,983 A | 2/1983 | Lichtenstein | |
| 4,445,174 A | 4/1984 | Fletcher | |
| 4,560,472 A * | 12/1985 | Granzow et al. | 210/140 |
| 4,574,283 A * | 3/1986 | Arakawa et al. | 340/3.51 |
| 4,695,944 A | 9/1987 | Zandveld et al. | |
| 4,707,778 A * | 11/1987 | Yamada et al. | 700/3 |
| 4,725,694 A | 2/1988 | Auer et al. | |
| 4,731,731 A * | 3/1988 | Cochran | 210/739 |
| 4,756,706 A | 7/1988 | Kerns et al. | |
| 4,796,634 A | 1/1989 | Huntsman et al. | |
| 4,823,256 A | 4/1989 | Bishop et al. | |

(Continued)

FOREIGN PATENT DOCUMENTS

| DE | 19849787 | 2/2000 |
|---|---|---|
| EP | 0306211 | 3/1989 |

(Continued)

OTHER PUBLICATIONS

International Search Report and Written Opinion for International Application No. PCT/US2009/046997 dated Feb. 16, 2010.

*Primary Examiner* — Justine Yu
*Assistant Examiner* — Larry R Wilson
(74) *Attorney, Agent, or Firm* — K&L Gates LLP

(57) ABSTRACT

A dialysis machine includes a control unit having a user interface; a heater(s) located separate from the control unit; a supervisory processor located with the control unit; a delegate control processor located with the heater(s), the delegate control processor in communication with the supervisory processor and configured to receive load cell, heater(s) plate and supply bag temperature sensor inputs; and a subdelegate heater(s) processor in communication with the control processor and configured to control power to the heater(s). The machine can also include primary and secondary monitoring processors that perform a safety check to the control processing and monitor the load cell.

21 Claims, 4 Drawing Sheets

(56) References Cited

U.S. PATENT DOCUMENTS

| | | | |
|---|---|---|---|
| 4,897,784 A | 1/1990 | Nay | |
| 4,990,258 A | 2/1991 | Bjare et al. | |
| 5,002,055 A * | 3/1991 | Merki et al. | 600/345 |
| 5,053,684 A | 10/1991 | Nooyen | |
| 5,186,609 A | 2/1993 | Inoue et al. | |
| 5,276,611 A | 1/1994 | Ghiraldi | |
| 5,319,363 A | 6/1994 | Welch et al. | |
| 5,326,476 A | 7/1994 | Grogan et al. | |
| 5,445,610 A * | 8/1995 | Evert | 604/29 |
| 5,472,614 A | 12/1995 | Rossi | |
| 5,487,827 A | 1/1996 | Peterson et al. | |
| 5,591,344 A | 1/1997 | Kenley et al. | |
| 5,609,770 A | 3/1997 | Zimmerman et al. | |
| 5,618,441 A | 4/1997 | Rosa et al. | |
| 5,620,608 A | 4/1997 | Rosa et al. | |
| 5,629,871 A | 5/1997 | Love et al. | |
| 5,759,044 A | 6/1998 | Redmond | |
| 5,784,547 A | 7/1998 | Dittmar et al. | |
| 5,788,851 A | 8/1998 | Kenley et al. | |
| 5,938,634 A * | 8/1999 | Packard | 604/29 |
| 6,052,752 A | 4/2000 | Kwon | |
| 6,137,776 A | 10/2000 | Bauerschmidt et al. | |
| 6,146,523 A | 11/2000 | Kenley et al. | |
| 6,151,298 A | 11/2000 | Bernhardsson et al. | |
| 6,595,948 B2 | 7/2003 | Suzuki et al. | |
| 6,676,621 B1 | 1/2004 | Menninger | |
| 6,868,309 B1 | 3/2005 | Begelman | |
| 6,880,034 B2 | 4/2005 | Manke et al. | |
| 7,152,469 B2 | 12/2006 | Milleker et al. | |
| 7,942,851 B2 * | 5/2011 | Faries et al. | 604/114 |
| 8,226,595 B2 * | 7/2012 | Childers et al. | 604/29 |
| 2003/0220605 A1 | 11/2003 | Bowman et al. | |
| 2003/0220609 A1 * | 11/2003 | Childers et al. | 604/29 |
| 2004/0039456 A1 * | 2/2004 | Davlin et al. | 700/3 |
| 2007/0112297 A1 * | 5/2007 | Plahey et al. | 604/28 |
| 2007/0276328 A1 | 11/2007 | Childers et al. | |
| 2008/0015493 A1 | 1/2008 | Childers et al. | |
| 2008/0177222 A1 * | 7/2008 | Roger | 604/29 |

FOREIGN PATENT DOCUMENTS

| | | |
|---|---|---|
| EP | 0428505 | 5/1991 |
| EP | 0432138 | 6/1991 |
| EP | 0491183 | 6/1992 |
| EP | 0611228 | 8/1994 |
| EP | 1 894 586 | 3/2008 |
| GB | 2282244 | 3/1995 |
| WO | 9014850 | 12/1990 |
| WO | 9966407 | 12/1999 |

* cited by examiner

DISTRIBUTED PROCESSING SYSTEM AND METHOD FOR DIALYSIS MACHINES

BACKGROUND

It is known to use delegating or cascading processing in medical systems, such as a dialysis system. The trend has been to use faster, more powerful processors, which can handle an increasing number of software related tasks. One drawback of faster processing is increased cost. Another drawback of faster processing is increased electromagnetic interference ("EMI"), which is particularly important in a medical environment.

Another consideration in distributed processing is the physical configuration of the medical machine. For example, a machine having a single housing for all components does not have cabling constraints. A machine having multiple components or discrete subassemblies, however, presents cabling issues. It is desirable to minimize electrical connections for ease of use and reliability.

There is, accordingly, a need to provide an effective, low cost, low EMI distributed processing system, and in particular, one that can mitigate the number of wire connections made between different discrete components of a medical machine or system.

SUMMARY

The distributed processing system and method are illustrated herein in connection with a gravity based peritoneal dialysis ("PD") machine that includes three physically separated units. First, a supply bag/heater(s) unit is provided that supports, weighs and warms dialysate supply bags. The supply bag/heater(s) unit is positioned at a higher elevation than the patient's peritoneum, so that gravity will pull fresh dialysate from the supply bags into the patient's peritoneum. Second, a main control unit operating a user interface is provided, which is positioned at approximately the same level as the patient and which controls therapy. Third, a machine base upon which rests a drain container is provided and positioned at a level below the patient, so that gravity will allow dialysate in the patient's peritoneum to fill the drain container. The machine base includes a load cell for weighing the drain container. The supply bag/heater(s) unit includes a load cell for weighing the supply bags.

The physical separation of the three units causes a separation of the electronics as well. Cabling is required to connect the separate units together. Due to the overall PD machine height, the unit is transported as separate units that are assembled prior to use. Similarly, each time the machine is to be transported, disassembly and reassembly is required. To facilitate ease of disassembly and reassembly, to reduce cost, and improve reliability, it is desirable to minimize the number of connections between the separate units.

The distributed processing architecture of the present disclosure divides processing tasks between a supervisory processor, safety processor, delegate processors and sub-delegate processors. Since the various processing tasks are distributed between multiple processing elements, the processing power required of each separate processor is less than the processing power that would be required with fewer processors. The disclosed configuration reduces the overall cost of the cumulative processing required and allows the use of lower processor clock speeds. Indeed, it is believed that the total cost of the processing elements remains approximately the same independent of the number used, assuming the processing power speed and memory are scaled properly.

The various processors are separated according to the separation of the physical units of the overall system. For example, the upper supply bag support and heater(s) carry with them the electronics local to such components. The supply bags are weighed to know how much supply remains. A load sensor is provided accordingly with the upper electronic subassembly. Bag heater(s) control requires temperature feedback. Temperature sensors are, therefore, also located with the upper, supply/heater(s) electronics. The middle, control unit includes the system's user interface ("UI"). The control unit electronics, accordingly, control the UI and provide supervisory and primary monitoring or safety processing for the whole system. The machine base unit supports and weighs a drain container. Accordingly, a drain fluid load sensor is provided with the machine base load cell electronics.

The upper, supply/heater(s) electronics are divided into two parts. A first set of electronics involves the sensors (temperature and load) and heater(s) elements that are located with bag support tray. In one embodiment, the first supply/heater(s) electronics are connected to or held by the supply bag tray and include three primary (control) and three secondary (monitoring) bag temperature sensors, three primary (control) and three secondary (monitoring) heater(s) plate temperature sensors, three resistive heating coils and a supply bag load cell.

A second set of supply/heater(s) electronics includes the local processors, associated analog to digital converters, and heater(s) power switching control. The second supply/heater(s) electronics components are attached to a printed circuit board ("PCB") carried by the supply/heater(s) unit, while the first supply/heater(s) electronics, as stated, are located physically at the tray.

The components of the second supply/heater(s) PCB interface with the components of the first supply/heater(s) electronics and the control unit electronics. There are in one embodiment a total of thirty-eight physical interconnecting wires between the first and second supply/heater(s) electronics due to the many sensors used. There are only six total physical interconnecting wires between the second supply/heater(s) subassembly and the control unit electronics. The second supply/heater(s) electronics are located accordingly with the first supply/heater(s) electronics, so that the thirty-eight physical connections between the supply/heater(s) electronic subassemblies can be made short and direct. Moreover, the connections are made during manufacture, e.g. via hardwires and do not require connectors (athough connectors can be used if desired) because the two units are both carried by the supply/heater(s) unit during assembly/disassembly of the PD system. The six connections between the second supply/heater(s) electronics and the control unit electronics require cabling that the user connects/disconnects during assembly/disassembly (e.g., via two cables, a first cable for four low voltage connections and a second cable for two AC power connections required by the heater) with a single connector on each end of each cable.

The second set of supply/heater(s) electronics includes three delegate processors, namely, a delegate control processor, delegate monitoring processor and a sub-delegate heater(s) processor. The delegate control processor includes a ten-bit analog-to-digital converter ("ADC") that is configured to read the temperature of the six primary or control temperature sensors mounted on the first supply/heater(s) electronics. The delegate control processor also reads a supply bag load cell of the first supply/heater(s) electronics via a twenty-four bit ADC.

The sub-delegate heater(s) processor controls, e.g., three, supply bag heater(s) of the first supply/heater(s) electronics.

The sub-delegate processor is located on the alternating current ("AC") line side of an isolation barrier and is, therefore, at AC line potential. The sub-delegate heater(s) processor communicates with the delegate control processor via an electrically isolated, optically coupled interface.

The delegate monitoring processor monitors the heater(s) plate and supply bag temperatures via separate, redundant sensors, namely, the six secondary bag and plate temperature sensors. The delegate monitoring processor also monitors the supply bag load cell of the first supply/heater(s) electronics via a second, redundant twenty-four bit ADC.

The control versus safety processing is split between the PCB of the second supply/heater(s) electronics and a PCB of the main control unit electronics. Separate safety monitoring provides enhanced safety, in which the primary function of the control processors is to control the machine, whereas, the primary function of the safety and monitoring processors is to monitor the sensors, redundantly, to verify proper operation and to shut down or place the machine into a safe state if necessary.

A main, supervisory/UI processor is provided with the control unit electronics. In addition to being the supervisory processor for the machine, the supervisory processor also controls the UI. In an alternative embodiment, the distributed processing architecture includes a separate delegate user interface processor that interfaces between the supervisory processor and the UI components (display, keypad, etc.).

The supervisory processor generates commands to delegate the tasks of supply bag solution heating, solution temperature monitoring, and supply bag weighing to the delegate control processor located with the second supply/heater(s) electronics. In turn, the delegate control processor delegates bag heater(s) control to the sub-delegate heater(s) processor also located on the second supply/heater(s) electronics. For example, when the supervisory processor wants to heat the supply bag dialysate solution, the supervisory processor sends a command over, e.g., a bi-directional single-wire universal asynchronous receiver/transmitter ("UART"), to the delegate control processor indicating a desired temperature of the solution. The delegate control processor reads the bag sensors located on the first supply/heater(s) electronics to determine if heating is required. If it is, the delegate control processor sends a command to the sub-delegate heater(s) processor to activate the one or more heater(s) element located with the first supply/heater(s) electronics.

The sub-delegate heater(s) processor also reads an AC voltage level signal from a detection circuit located on the second supply/heater(s) electronics to determine which heater(s) switches should be triggered (based on AC voltage level). The sub-delegate heater(s) processor then activates the corresponding switches to heat one or more of the supply bags as requested.

The delegate control processor monitors the plate and bag temperature sensors to close a control loop with the sub-delegate heater(s) processor and heat and maintain the bag(s) solution to and at the desired temperature. The delegate control processor also continuously monitors the supply bag load cell and reports a corresponding bag weight to the supervisory processor.

The delegate monitoring or safety processor of the second supply/heater(s) electronics also monitors the plate temperatures, bag temperatures and the bag weight and reports this information to a main monitor/safety processor located with the control unit electronics via a second, separate serial link, e.g., a second single-wire UART. Information from the delegate control processor reported to the supervisory processor is in turn communicated from the supervisory processor to the safety processor via a third serial link, e.g., a third single-wire UART connection, between the supervisory and safety processors both located with the control panel. If the two temperature readings sent to the safety processor do not agree, the safety processor has the capability to cut power to the heater (s) switches and elements, e.g., via a mechanical relay. Likewise, if supply bag weight signals sent to the safety processor do not agree, the safety processor can force a closure of supply fluid line pinch valves that are normally under control of the supervisory processor, which shuts off solution flow from the supply bags to the patient.

The control unit electronics also includes a sub-delegate power processor, which controls an on/off state of the PD system. The sub-delegate power processor is, in one embodiment, a low-end, very low-power and low-cost processor, which is powered at all times, so that the power-on function can be controlled when the rest of the machine is not powered. Such arrangement allows the power switch to be a simple, low-cost, (e.g., membrane type) pushbutton, eliminating the need for a more costly mechanical power switch. The power arrangement also allows either the supervisory processor or the sub-delegate power processor to initiate a power-off command.

In the particular gravity-fed PD system example below, there is no sub-processing element associated with the base or drain load cell electronics because the only electrical component of the drain load cell electronics is a load cell having only five connections. Thus, a separate delegate processor would not provide a significant advantage over a direct connection. However, if the third subassembly had more electrical components, it could have one or more sub-delegate processors.

The three units of the PD assembly are connected electrically together via three cables in one embodiment. A first cable carries four wires for low-voltage interconnect between the supply/heater(s) electronics and the control unit electronics. A second cable caries two wires for AC mains voltage interconnect between the supply/heater(s) electronics and the control unit electronics. It is contemplated to reduce the first and second cables to a single cable if the low versus high voltage wires are properly isolated from one another. A third cable carries five low voltage wires between the drain load cell and the control unit electronics. Electrical connection is made via plug-in connectors located at each end of each cable, except for the drain load cell connection that has only a single connector for connection to the control unit, with the connection to the load cell being integral to the load cell.

A power plug to the control unit is also provided, which ultimately supplies power to each electrical component of the three electronic subassemblies. Thus assembling/disassembling the PD system electrically is a relatively easy task. In an alternative embodiment, the main AC power cable runs to the base or drain unit instead of to the control unit. Here, there is an additional two wire cable connection made between the base and control units to route the AC supply from the base unit to the control unit.

It is accordingly an advantage of the distributed processing system of the present disclosure to distribute the processing to fit physical system restraints, to replace hard-wiring with communication links, and to use lower-powered, less expensive processors.

It is another advantage of the distributed processing system of the present disclosure to provide a medical system that is readily assembled and disassembled electrically.

It is a further advantage of the distribution processing system of the present disclosure to provide an electrical system having distributed processing that reduces the overall number of and length of electrical wires, improving safety and reliability.

Additional features and advantages are described herein, and will be apparent from the following Detailed Description and the figures.

DETAILED DESCRIPTION

Figure 1:
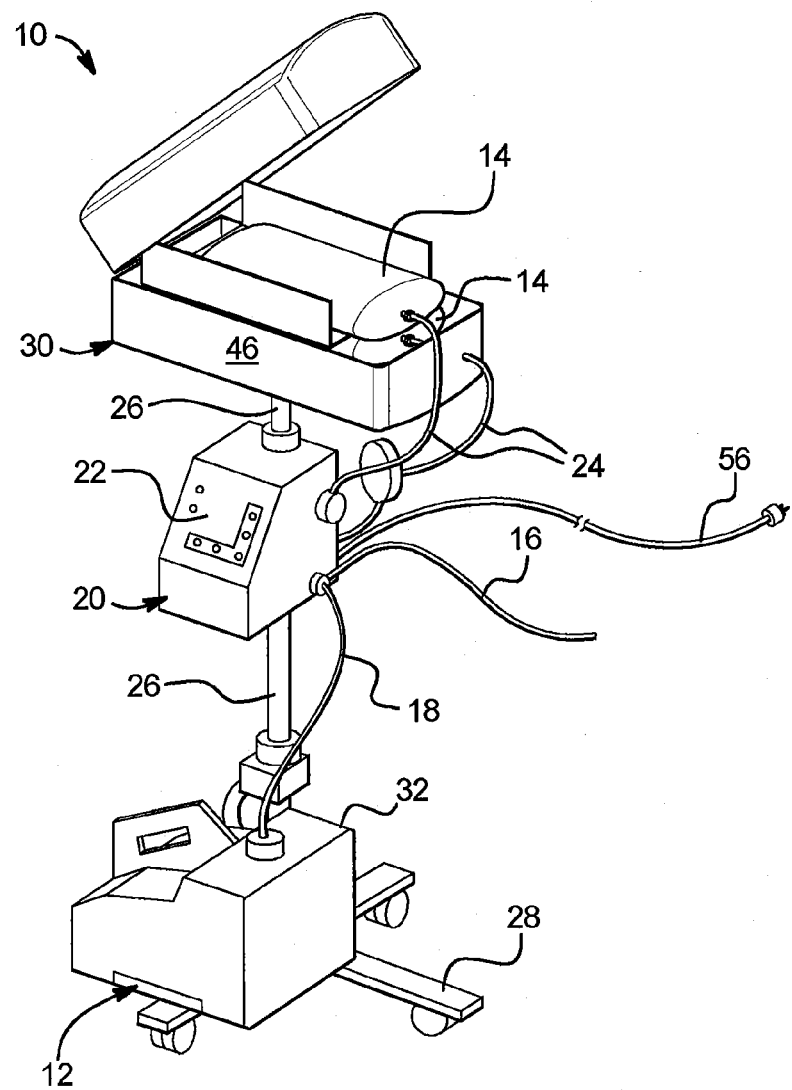
FIG. 1 is a perspective view of one embodiment of a medical system, having physically separated units, which employ the distributed processing system and method of the present disclosure.

Referring now to the drawings and in particular to FIG. 1, system 10 illustrates one embodiment of the present disclosure. System 10 in the illustrated embodiment is an automated peritoneal dialysis ("APD") system. Various techniques have been developed to monitor the amount of dialysate delivered to and removed from the patient as well as amount of the patient's body fluid or ultrafiltrate, which is also removed from the patient undergoing APD. In the illustrated embodiment, system 10 operates with a load cell machine base 12. The load cell machine base is discussed in more detail below in connection with FIG. 2. It should be appreciated however that the distributed processing system discussed herein can operate with APD systems having volumetric control systems other than load cells. Further, the distributed processing system can operate with other types of dialysis or blood filtration systems, such as systems for hemodialysis ("HD"), hemofiltration ("HF"), hemodiafiltration ("HDF"). The system can be used with other types of medical delivery systems and is particularly well-suited for systems that involve physically separated components, such as system 10.

System 10 also includes a control unit 20, which includes a control panel 22 allowing the operator or patient to set, begin and monitor treatment. Control unit 20 also includes valve and/or pump actuators that operate with disposable fluid tubes to distribute medical fluid, such as dialysate to a desired destination. Control unit 20 in one embodiment operates with pinch valves that pinch various parts of a tubing set to control the flow of fresh and spent dialysate to a desired destination. Alternatively, control unit 20 operates a disposable cassette, which can include cassette sheeting that is selectively closed against or opened from rigid valve at various places to produce a desired valve state. Control unit 20 can include a plurality of pumps for pumping dialysis fluid to and from a patient or dialyzer.

In the illustrated embodiment, the instrument uses a pump or gravity to feed fresh fluid from a supply bag 14 to the patient through a patient line 16 and uses a pump or gravity to feed spent or effluent fluid from the patient to a drain container 32 via a pump (not illustrated) located within control unit 20 via a drain line 18. Supply bags 14 are located on a supply bag/heater(s) unit 30, which can be a resistive type heater(s). Supply bag/heater(s) unit 30 heats dialysate to a desirable temperature for treatment, such as 37° C. Fluid flows from supply bags 14 and supply bag/heater(s) unit 30 via a pump or gravity through a supply line 24 from each supply bag 14 to control unit 20. When a certain one or more valve is open, the heated fluid from supply line 24 flows through the disposable, including patient line 16, to the patient.

As discussed above, the amount of effluent fluid flowing from the patient to drain container 32 through drain line 18 is weighed at load cell machine base 12. That weight can be compared against a known weight of supply bags 14 to determine an amount of ultrafiltrate ("UF") that has been removed from the patient. Alternatively, control unit 20 can include a weigh scale that weighs the amount of fresh fluid contained in supply bags 14. Here, a controller within control unit 20 subtracts the beginning weight of fluid in supply bags 14 from the weight of fluid collected in container 32 to determine the amount of UF removed from the patient. One system and method for operating system 10 is discussed in copending patent applications entitled: "Automated Dialysis System Driven By Gravity And Vacuum", filed May 26, 2006, Ser. No. 11/420,608, the entire contents of which are incorporated herein expressly by reference and relied upon.

Figure 2:
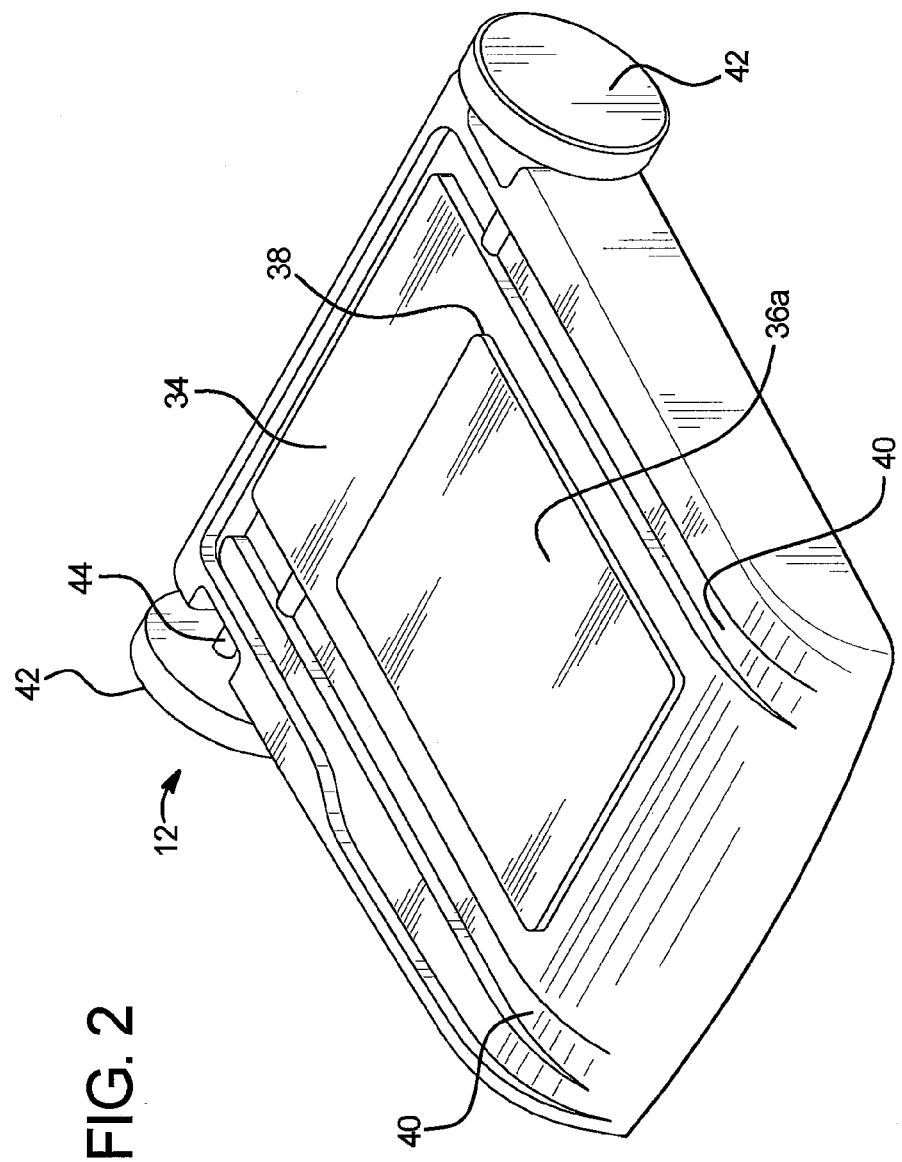
FIG. 2 is a perspective view of one embodiment of a machine base unit for the system of FIG. 1, which has a drain container load cell.

Referring additionally to FIG. 2, load cell subassembly 12 illustrates one suitable load cell for use with system 10. Subassembly 12 includes a platform 34 that surrounds a load cell 36a, which floats within a cutout 38 of platform 34. Platform 34 further includes or defines wheel tracks 40, which are sized in width to accept the wheels of a drain container or assembly holding the drain container 32.

FIG. 1 illustrates one embodiment in which load cell subassembly 12 is placed above wheeled base 28. System 10 also includes a stand 26, which is connected to wheeled base 28, which allows system 10 to be grabbed and moved within the patient's house or within a center or hospital. Load cell subassembly of FIG. 2 illustrates an alternative embodiment in which subassembly 12 itself rests on the ground. Subassembly 12 accordingly includes wheels 42, which connect to an axle 44, which in turn is coupled rotatably to platform 34 of load cell subassembly 12. In this manner, the patient can roll subassembly 12 with or without a supported drain container 32 when the patient needs to move the entire medical fluid treatment system 10.

As illustrated in FIG. 1, support tray/heater(s) unit 30 supports, weighs and warms dialysate supply bags 14. Support tray/heater(s) unit 30 is held at a higher elevation than the patient's peritoneum in the illustrated embodiment, so that gravity will pull dialysate from supply bags 14 to fill the patient's peritoneum. Support tray/heater(s) unit 30 forms a first subassembly of system 10.

Control unit 20, which is the main control unit for system 10, is positioned at approximately the same level as the patient and controls the therapy. Control unit 20 forms a second subassembly of system 10.

Load cell subassembly 12 (either embodiment discussed above), which supports drain container 32 is provided and positioned at a level below the patient, so that gravity will pull spent dialysate from the patient's peritoneum into drain container 32 for weighing via load cell 36a. Load cell subassembly 12 forms a third subassembly of system 10.

The physical separation of the three separate units 12, 20 and 30 causes a separation of the electronics as well. Cabling, which can be run through tubular support 26, connects separate units 12, 20 and 30 together electrically. Due to the overall machine height of system 10 (e.g., 1.1 meters), the system is shipped disassembled as three separate units 12, 20 and 30 that are assembled prior to use. Similarly, each time the system 10 is to be transported, disassembly and reassembly of units 12, 20 and 30 is required. To facilitate ease of disassembly and reassembly, to reduce cost, and improve reliability, system 10 has minimized the number of connections between units 12, 20 and 30 via distributed processing system 100 and associated methodology discussed in connection with FIG. 3.

Figures 3, 3A:
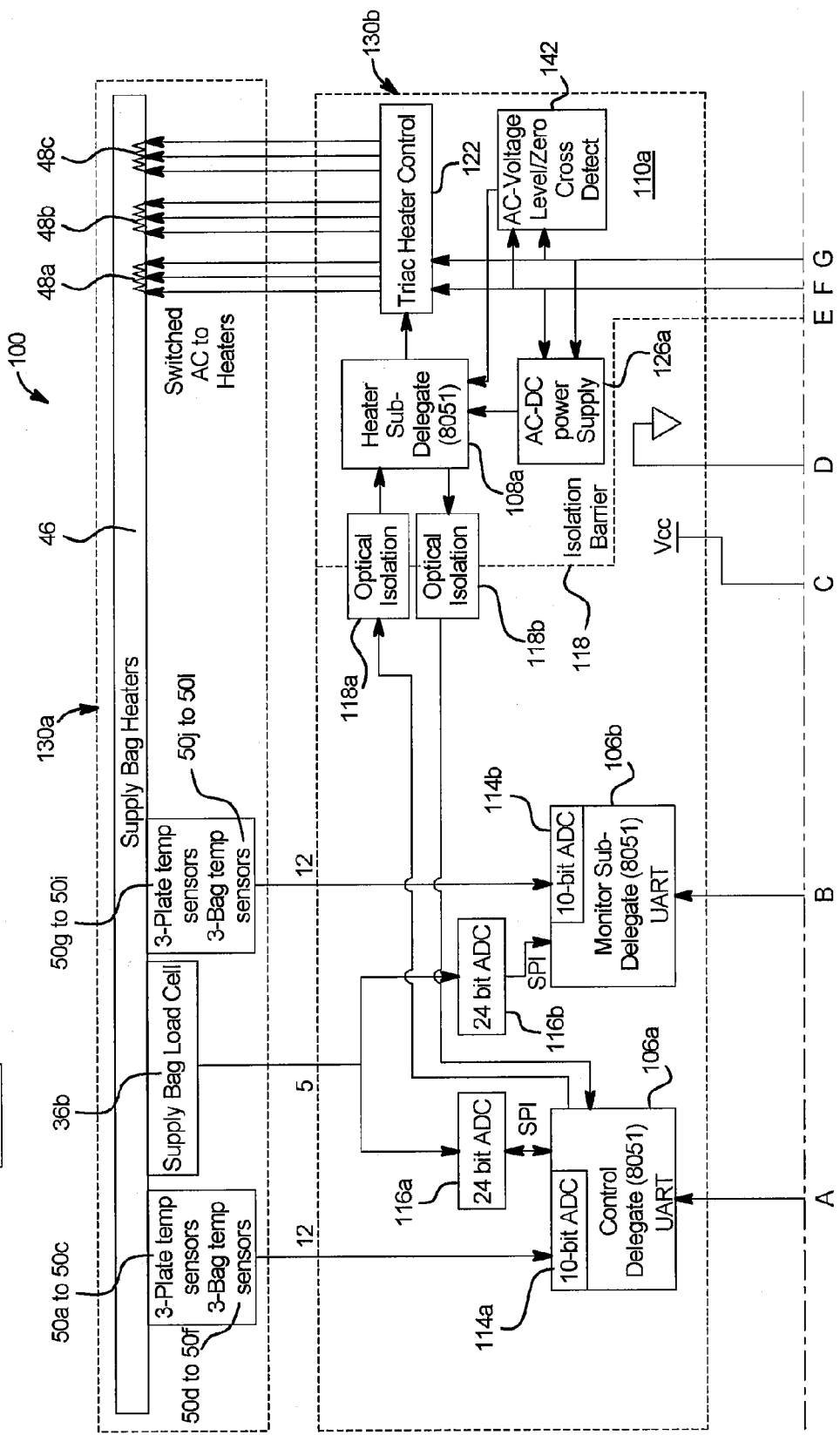
FIG. 3 (referring collectively to FIG. 3A and FIG. 3B) is a schematic view of one embodiment of the distributed processing system and method of the present disclosure.
Figure 3B:
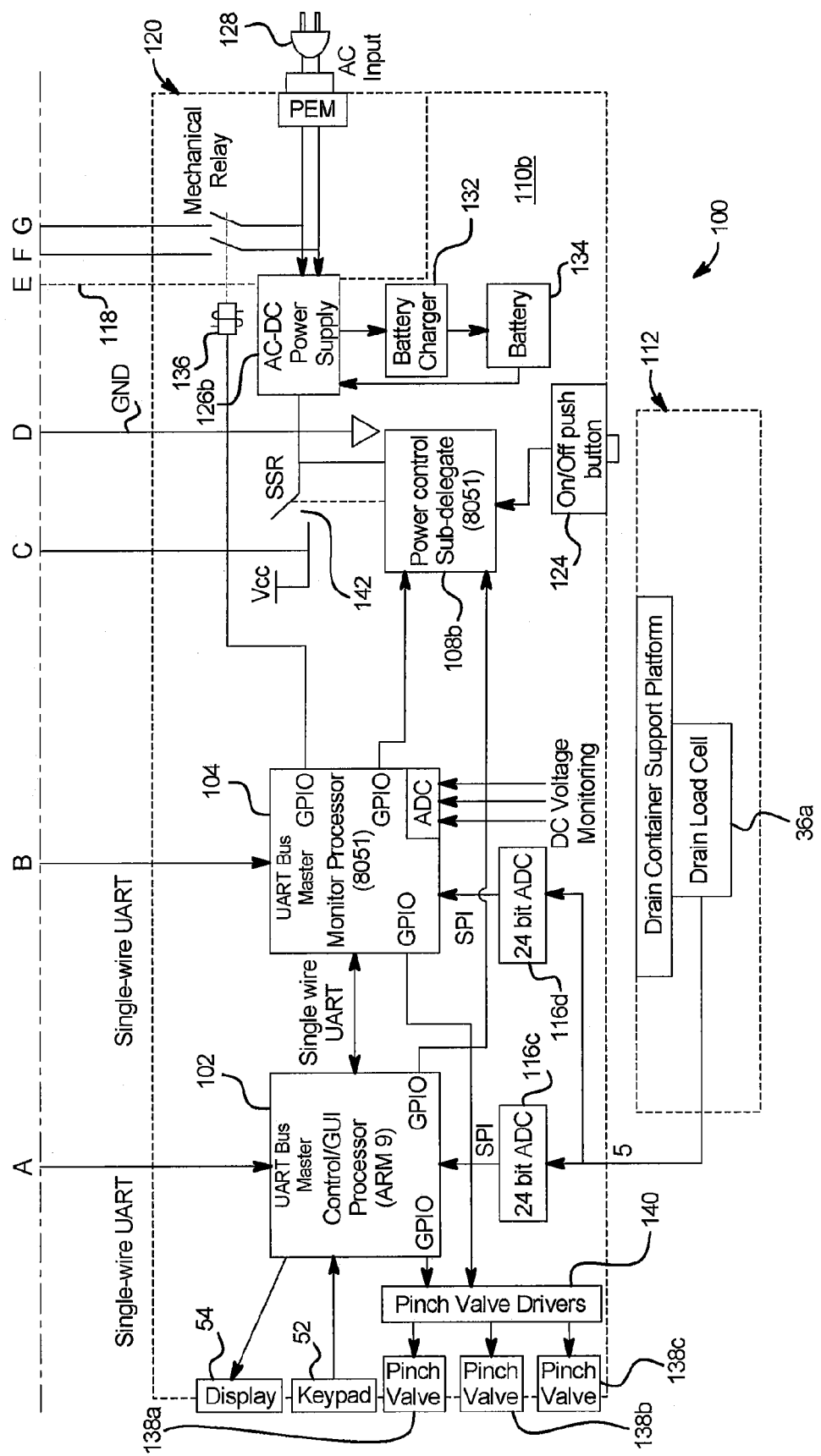

Referring additionally to FIG. 3, the distributed processing system 100 of the present disclosure divides processing tasks between three electrical subassemblies, namely, control unit electronics 120, supply/heater(s) electronics 130 and drain load cell electronics 112, respectively. Supply/heater(s) electronics 130 are split into two subassemblies 130a and 130b as illustrated. Electrical subassemblies 120, 130 (referring collectively to supply/heater(s) subassemblies 130a and 130b) and 112 split the processing for system 10 amongst master processing, safety processing, delegate processing and sub-delegate processing.

Since the various processing tasks are distributed between multiple processing elements of system 100, the processing power required of each separate processor is less than the processing power that would be required with fewer processors. Distributed processing system 100 reduces the overall cost of the processing for system 10 and allows the use of processors having lower processor clock speeds. The total cost of the processing elements remains approximately the same virtually independent of the number used, assuming the processing power speed and memory are scaled properly. In the illustrated case of the gravity-fed PD system 10, distributed processing system includes a total of six processing elements, namely, supervisory and UI control processor 102, a primary monitoring or safety processor 104, delegate heater (s)/supply processors 106a and 106b, a sub-delegate heater(s) processor 108a and a sub-delegate power processor 108b. At the low processing end, sub-delegate processors 108 (referring collectively to sub-delegate processors 108a and 108b) cost less than $1.00 US in production quantities as of the filing date of this application.

As illustrated in FIG. 3, first supply bag/heater(s) electronics 130a is coupled directly or indirectly to a supply bag support tray 46 and includes components such as, three heater (s) elements 48a to 48c, three primary heater(s) plate temperature sensors 50a to 50c, three primary bag temperature sensors 50d to 50f, three secondary or monitoring heater(s) plate temperature sensors 50g to 50i, and three secondary or monitoring heater(s) bag temperature sensors 50j to 50l. Bag support tray 46 also supports, couples to or is otherwise configured with a supply bag load cell 36b, which weighs one or more supply bag 14 (FIG. 1).

Second supply/electronics 130b includes a printed circuit board ("PCB") 110a. Electrical components fixed to PCB 110a interface with the electrical components of the first supply bag/heater(s) electronics 130a (which are generally fixed to or carried by support tray 46) and also with components of control unit electronics 120, which is provided on a second PCB 110b located within control unit 20.

In one example, there are a total of thirty-eight physical interconnecting wires between the supply/heater(s) electronics 130a and 130b and a total of six physical interconnecting wires between the second supply/heater(s) electronics 130b and the control unit electronics 120. Second supply/heater(s) electronics 130b are located accordingly with the first supply/heater(s) electronics 130a, within supply/heater(s) unit 30, so that the thirty-eight physical connections between electronic subassemblies 130 are made short and direct. Further, the connections are made once during manufacture, e.g., via traces on circuit board 110a or via hardwires and do not require patient disconnection and connection to transport PD system 10.

The, e.g., six electrical connections between second supply/heater(s) electronics subassembly 130b and the control unit electronics 120 require cabling that the user connects/disconnects during assembly/disassembly. Such connection and disconnection can be made via a single plug-in connector due to the relatively limited number of wires between second supply/heater(s) electronics 130b and the control unit electronics 120. Alternatively, high and low voltage wires are separated into two plug-in type cables.

As seen in FIG. 3, second supply/heater(s) electronics 130b includes two delegate processors, namely, a delegate control processor 106a and a delegate monitoring processor 106b. Second supply/heater(s) electronics 130b also includes sub-delegate heater(s) processor 108a. Each of delegate supply/heater(s) processors 106a, 106b and 108a is soldered to PCB 110a in one embodiment.

Delegate control processor 106a includes a ten-bit analog-to-digital converter ("ADC") 114a that is configured to read the temperature of the three control plate temperature sensors 50a to 50c and three control bag temperature sensors 50d to 50f of first supply/heater(s) electronics 130a, which is mounted to tray 46 of supply/heater(s) unit 30. Delegate control processor 106a also reads supply bag load cell 36b of the first supply/heater(s) electronics 130a via a twenty-four-bit ADC 116a.

Heater(s) sub-delegate processor 108a controls the three supply bag heater(s) 48a to 48c of the first supply/heater(s) electronics 130a, which is coupled to tray 46 of supply/heater (s) unit 30. Heater(s) sub-delegate processor 108a is on the alternating current ("AC") line side of an isolation barrier 118 (separating AC from direct current ("DC") components), and is, therefore, at AC line potential. Isolation barrier 118 includes a pair of optical isolators 118a and 118b. Heater(s) sub-delegate processor 108a communicates with control delegate processor 106a via optical isolators 118a and 118b as illustrated but can send control signals directly to heater(s) switch controller 122.

Locating processor 108a on AC line side of side isolation barrier 118 enables the use of only two digital optical isolators 118a and 118b. If processor 108a was located on the DC side, the various control outputs and monitoring inputs to heater(s) sub-delegate processor 108a would have to be galvanically isolated from the AC side. Such isolation would then need to be applied to AC-voltage detection output, zero cross inputs, and Triac control outputs, resulting in the use of many isolators and increased cost.

AC power via plug 128 powers both AC to DC power supplies 126a and 126b and heater(s) switch controller 122. Each PCB 110a and 110b of electronic subassemblies 130b and 120, respectively, uses one of the AC to DC power supplies, 126a and 126b, respectively. AC to DC power supply 126a supplies DC power to heater(s) sub-delegate processor 108a. AC to DC power supply 126b supplies DC power to battery charger 132, which charges back-up battery 134. Back-up battery 134 can supply power to Vcc for electrical subassemblies 120 and 130b for a limited period should AC power at plug 128 fail or be removed. AC to DC power supply 126a also supplies DC power, here, to each electrical component on the DC side of isolation barrier 118 for both PCB's 110a and 110b of electronic subassemblies 130b and 120, indicated generally by Vcc. A Vcc line is run accordingly between subassemblies 130b and 120. Likewise, a return or ground line ("GND") is run between assemblies 130b and 120.

Delegate monitoring processor 106b monitors the heater(s) plates and supply bag temperatures via separate, redundant temperature sensors 50g to 50l and includes a ten-bit analogto-digital converter ("ADC") 114b that is configured to read the temperature of the three redundant plate temperature sensors 50g to 50i and the three redundant bag temperature sensors 50j to 50l of first electrical supply/heater(s) electronics 130a. Delegate monitoring processor 106b also reads a redundant signal from supply bag load cell 36b of the first supply/heater(s) electronics 130a via a twenty-four-bit ADC 116b. The redundant signal is sent alternatively from a separate, redundant supply bag load cell 36b (not shown), which can be mounted directly adjacent to the illustrated supply bag load cell 36b.

The controlling and monitoring functionality on PCB 110a of second supply heater(s) electronics 130b and on the PCB 110b of the control unit electronics 120 provide for enhanced reliability. Here, the primary function of the control processors is to control the machine, whereas the primary function of the monitoring processors is to monitor the machine and the control processor to verify proper operation.

Supervisory and UI control processor 102 is provided on PCB 110b of control unit electronics 120. Supervisory processor 102 in one embodiment employs advanced RISC machine ("ARM") architecture, which is a thirty-two-bit processor having power saving features to achieve low power consumption, which is desirable for PD system 10. In addition to being the supervisory processor for the system 10, supervisory processor 102 also controls the user interface, including control panel 22 having a keypad 52 and display 54. In an alternative embodiment, distributed processing architecture 100 includes a separate user interface delegate processor interfacing between main supervisory processor 102 and the user interface equipment 22, 52 and 54.

Main control processor 102 delegates the tasks of supply bag solution heating, solution temperature monitoring, and supply bag weighing to delegate control processor 106a located on the second supply/heater(s) electronics 130b. In turn, the delegate control processor 106a delegates bag heater (s) control to the sub-delegate heater(s) processor 108a also located on the second supply/heater(s) electronics 130b.

For example, when the supervisory processor 102 wants to heat the supply bag dialysate solution, the supervisory processor sends a command over a first serial link, such as a bi-directional single-wire universal asynchronous receiver/transmitter ("UART") link, to the delegate control processor 106a indicating the desired temperature of the solution. Delegate control processor 106a reads the bag temperature sensors 50d to 50f located on first supply/heater(s) electronics 130a to determine if heating is required. If it is, delegate control processor 106a sends a command to the sub-delegate heater(s) processor 108a to activate one or more of heater(s) elements 48a to 48c of first supply bag/heater(s) electronics 130a.

Sub-delegate heater(s) processor 108a then reads AC-Voltage level information from an AC-Voltage Level/Zero-Cross detect circuit 142 located on the second supply/heater(s) electronics 130b to determine which switching devices, e.g., TRIode for alternating current ("Triac's") 122, should be triggered (based on AC voltage level). Sub-delegate heater(s) processor 108a then activates the Triac(s) 122 at the zero voltage crossing point of the AC waveform indicated by the zero cross detect circuit 142. A universal heater(s) using circuit 142 and switching or Triac(s) controller 122 is described in co-pending patent application Ser. No. 12/035,991, entitled "Machine Having Multiple Line Voltage Heater," filed Feb. 22, 2008, assigned to the assignee of the present application, the pertinent portions of which are incorporated herein by reference.

In one embodiment, both activate and deactivate heater(s) commands are sent from delegate control processor 106a to the sub-delegate heater(s) processor 108a, depending upon current plate and solution temperatures. Other commands can be sent periodically requiring a response from heater(s) sub-delegate processor 108a, e.g., health status request, software version request. There can also be unsolicited messages from the heater(s) sub-delegate processor 108a to delegate control processor 106a indicating various sensed conditions. These can, alternatively, be encoded into a response to a health status request from delegate control processor 106a.

Delegate control processor 106a also monitors the plate and bag temperature sensors 50a to 50f to close a control loop, causes sub-delegate heater(s) processor 108a to heat the bag solution to the correct temperature set at supervisory processor 102 and maintains the temperature at the desired temperature. The delegate control processor 106a also continuously monitors the supply bag load cell 36b and reports a corresponding bag weight to supervisory processor 102.

Delegate monitoring processor 106b of second supply/heater(s) electronics 130b also monitors the plate temperatures via sensors 50g to 50i, bag temperatures via sensors 50j to 50l, and the bag weight via load cell 36b and reports the sensed information to a safety processor 104 of control unit electronics 120 via a second serial link (e.g., a second single-wire UART link) as illustrated in FIG. 3. Information from the delegate control processor 106a reported to the supervisory processor 102 is in turn communicated from the supervisory processor 102 to the safety processor 104 via a third serial link (e.g., a third single-wire UART link) between supervisory and safety processors 102 and 104 located on main electrical subassembly 120.

If, for example, one or more of the plate temperatures from sensors 50a to 50c does not match corresponding temperatures from one or more of secondary plate sensors 50g to 50i, safety processor 104 has the capability to cut power to the heater(s) via a mechanical relay 136, which cuts all AC power to second supply/heater(s) electronics 130b at PCB 110a. Likewise, if the supply bag weight comparison of the separate signals sent from load cell 36b to safety processor 104 does not agree, the safety processor can also force a closure of pinch valves 138a to 138c via a pinch valve driver 140, which is normally under supervisory processor control, to stop solution flow from the supply bags 14 to the patient line 16.

Control unit electronics 120 also include a power control sub-delegate processor 108b, which is used to control an on/off state of the PD system 10. Sub-delegate power processor 108b in one embodiment is a low-end, low-power and low-cost controller, such as a Philips P87LPC767 processor or a Microchip PIC16F688 processor, which is powered at all times, so that a power-on function can be controlled when the rest of the PD system 10 machine is powered off. The power arrangement of system 10 allows a power switch 124 in electrical communication with sub-delegate power processor 108b to be a simple, low-cost (e.g., membrane type) switch, rather than a more costly, mechanical power switch.

The power arrangement of control unit electronics 120 also allows either supervisory processor 102 or the safety processor 104 to initiate a power-off command to the sub-delegate power control processor 108b, causing power control sub-delegate processor 108b to open SSR 142, which cuts the DC supply voltage Vcc to both PCBs 110a and 110b and associated electrical subassemblies 130b and 120 (except the to power control sub-delegate processor 108b). Removal of the DC supply voltage Vcc also causes the mechanical relay 136 to open, which effectively shuts off the machine.

In the gravity-fed PD system 10 of FIGS. 1 and 2 and associated processor architecture 100 of FIG. 3, there is no sub-processing element associated with the drain load cell electronics 112 because the only electrical component of electronics 112 is drain container load cell 36a having five electrical wires fed to each of twenty-four-bit ADC's 116c and 116d of control unit electronics 120. Twenty-four-bit ADC's 116c and 116d output respectively to supervisory and safety processors 102 and 104. In architecture 100, a separate sub-delegate processor provided with drain load cell electronics 112 would not provide a significant advantage over the direct electrical connections shown, which can be handled via a single connector carrying five wires. However, if drain load cell electronics 112 alternatively includes additional sensors, such as additional load cell sensors, drain fluid conductivity sensors, or drain container position sensors, the corresponding additional wires could justify the addition of a delegate processor provided at load cell electronics 112.

Distributed processing system 100 potentially reduces the electrical connections between machine units 30, 20 and 12 to two or three cables, e.g., one carrying six wires (two serial communication wires, a DC power Vcc wire, a DC GND wire, and two AC power wires) between units 20 and 30, and a second carrying five wires (five load cell signal wires) between control unit 20 and machine base 12. Both cables terminate in simple plug-in connectors that make electrical assembly and disassembly of PD system 10 easy, reliable and safe. In an alternative embodiment, there are two cables connecting units 20 to 30 (the two AC power wires are carried in a separate cable connection). Further alternatively, the AC input cable 56 is routed to control unit 20 via base or drain unit 12, resulting in a second AC cable connection between those units 12 and 20. Regardless, the vast majority of signal wires are short, making them less prone to noise. The multiple uses of distributed, point-of-use processing in system 100, reduces power used, noise produced and cost, but still allows for redundant, reliable control and safety.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis machine comprising:
a control unit having a user interface;
a heater located separate from the control unit;
a supervisory processor located with the control unit;
a delegate control processor located with the heater, the delegate control processor in communication with the supervisory processor and configured to receive a heater temperature sensor input; and
a programmable sub-delegate heater processor which reads information stored on at least one memory device, the sub-delegate heater processor in communication with the delegate control processor and configured to control power to the heater using the information stored on the at least one memory device in response to a command that is (i) received from the delegate control processor and (ii) generated based upon the heater temperature sensor input.

2. The dialysis machine of claim 1, wherein the delegate control processor and the sub-delegate heater processor are located on a same printed circuit board.

3. The dialysis machine of claim 1, which includes a load cell located with the heater, the delegate control processor further configured to receive a signal from the load cell.

4. The dialysis machine of claim 1, the delegate control processor galvanically isolated from at least one of the supervisory processor and the sub-delegate heater processor.

5. The dialysis machine of claim 1, the supervisory processor further configured to control at least one of: a keypad of the user interface, a display of the user interface and a valve driver of the user interface.

6. The dialysis machine of claim 1, which includes a primary monitoring processor in communication with the supervisory processor and with a delegate monitoring processor, the delegate monitoring processor configured to receive a heater temperature sensor input.

7. The dialysis machine of claim 6, the heater temperature sensor input to the delegate monitoring processor being the same as the heater temperature sensor input to the delegate control processor.

8. The dialysis machine of claim 6, the primary monitoring processor configured to cut power to the heater when the heater temperature sensor input to the delegate monitoring processor is different than the heater temperature sensor input to the delegate control processor.

9. The dialysis machine of claim 6, the delegate control processor and delegate monitoring processor each further configured to receive a load cell signal, the primary monitoring processor configured to affect a valve driver when the load cell signal to the delegate monitoring processor is different than the load cell signal to the delegate control processor.

10. The dialysis machine of claim 9, the load cell signal to the delegate monitoring and control processors sent from the same load cell or from a separate, redundant load cell.

11. The dialysis machine of claim 6, at least one of the supervisory and primary monitoring processors in further communication with a power control processor, the sub-delegate heater processor receiving an on/off switching signal from the at least one of the supervisory and primary monitoring processors.

12. The dialysis machine of claim 11, wherein at least one of the delegate control processor, the sub-delegate heater processor, the primary and delegate monitoring processors and the power control processor is a low level operating processor.

13. The dialysis machine of claim 6, the primary monitoring processor located with the supervisory processor, the delegate monitoring processor located with the delegate control processor.

14. The dialysis machine of claim 1, which includes a drain container located separate from the control unit, the supervisory processor configured to receive a load cell signal from a load cell located with the drain container.

15. A dialysis machine comprising:
a control unit having a first housing, the control unit including a user interface and at least one processor; and
a heater unit having a second housing, separate from the first housing, the heater unit including a heater/sensor subassembly and a processor subassembly, each subassembly including at least one processor, the heater/temperature subassembly further including a heater and a temperature sensor, the at least one processor of the control unit electrically connected to the at least one processor of the processor subassembly, the subassemblies connected via heater power and signal wires, the processor subassembly connected to the control unit via data transmission lines and power supply lines only, the at least one processor of the heater/sensor subassembly programmed to control the heater by reading information stored on at least one memory device in response to a command that is (i) received from the at least one processor of the processor subassembly and (ii) generated based upon a reading from the temperature sensor.

16. The dialysis machine of claim 15, wherein the at least one processor of the control unit includes a supervisory processor in communication with a user interface processor, the user interface processor operating the user interface.

17. The dialysis machine of claim 15, which further includes a drain unit, the drain unit connected to the control unit via at least one signal line.

18. The dialysis machine of claim 15, the control unit and the heater unit mounted separately from one another, wherein the second housing is located elevationally above the first housing to allow for a gravity patient fill.

19. A dialysis machine comprising:
a primary control processor;
a secondary control processor in communication with the primary control processor and programmed to accept a desired temperature command from the primary control processor;
a temperature sensor configured to input a sensed temperature input to the secondary control processor; and
a heater processor programmed to operate a heater by reading information stored on at least one memory device, the secondary control processor programmed to send or activate heater commands to the heater processor upon accepting the desired temperature command if a desired temperature of the desired temperature command is greater than an actual temperature of the actual temperature input, the heater processor configured to operate the heater using the information stored on the at least one memory device in response to a command that is (i) received from the secondary control processor and (ii) generated based upon the temperature input.

20. The dialysis machine of claim 19, the temperature sensor being one of a heater plate sensor and a dialysate bag sensor.

21. The dialysis machine of claim 19, which includes at least one different type of sensor inputting to the secondary control processor.

* * * * *